United States Patent
McDonel et al.

(10) Patent No.: US 9,670,146 B2
(45) Date of Patent: Jun. 6, 2017

(54) ON-LINE ANALYSIS OF ACRYLONITRILE PRODUCT

(71) Applicant: INEOS EUROPE AG, Rolle, Vaud (CH)

(72) Inventors: Timothy Robert McDonel, Elburn, IL (US); Jay Robert Couch, Naperville, IL (US); David Rudolph Wagner, Naperville, IL (US); Paul Trigg Wachtendorf, Victoria, TX (US)

(73) Assignee: Ineos Europe AG, Rolle (CH)

( * ) Notice: Subject to any disclaimer, the term of this patent is extended or adjusted under 35 U.S.C. 154(b) by 0 days.

(21) Appl. No.: 14/710,710

(22) Filed: May 13, 2015

(65) Prior Publication Data
US 2015/0329480 A1    Nov. 19, 2015

(30) Foreign Application Priority Data
May 19, 2014   (CN) .......................... 2014 1 0210100

(51) Int. Cl.
G05D 11/08   (2006.01)
C07C 253/32  (2006.01)
G05D 11/13   (2006.01)

(52) U.S. Cl.
CPC ............ *C07C 253/32* (2013.01); *G05D 11/13* (2013.01); *G05D 11/138* (2013.01)

(58) Field of Classification Search
USPC ............................................ 422/62; 558/462
See application file for complete search history.

(56) References Cited

U.S. PATENT DOCUMENTS

| 3,185,636 A | 5/1965 | Stevens et al. |
| 6,296,739 B1 | 10/2001 | Godbole |
| 6,355,828 B1 | 3/2002 | Rogers et al. |
| 2009/0223804 A1 | 9/2009 | Basham et al. |

FOREIGN PATENT DOCUMENTS

| CN | 101959850 | 1/2011 | |
| CN | 102199105 | 9/2011 | |
| CN | 103483222 | 1/2014 | |
| GB | 2176026 | 12/1986 | |
| JP | WO 2007132926 A1 * | 11/2007 | .............. B01J 29/40 |
| JP | 2012077041 A * | 4/2012 | |
| WO | 2009111605 | 3/2009 | |

OTHER PUBLICATIONS

English Machine Translation of Kobayashi JP 2012077041 A (Apr. 19, 2012) obtained from <https://worldwide.espacenet.com> on Aug. 6, 2016.*
Supplemental English Machine Translation of Kobayashi JP 2012077041 A (Apr. 19, 2012) obtained from <https://aipn.j-platpat.inpit.go.jp/> on Aug. 8, 2016.*
Crews et al. Organic Structure Analysis. New York, Oxford University Press, 1998, pp. 1-2.*
Bradzil, J. F. Kirk-Othmer Encyclopedia of Chem. Tech. 2010, 1-17.*

* cited by examiner

*Primary Examiner* — Michael Barker
*Assistant Examiner* — Amanda L Aguirre
(74) *Attorney, Agent, or Firm* — David P. Yusko

(57) ABSTRACT

An apparatus comprises a first controller configured to control at least the flow rate of a polymerization inhibitor or acrylonitrile product to a first location where the two are mixed. The apparatus comprises a first on-line analyzer configured to measure polymerization inhibitor concentration in the acrylonitrile product at a second location, the second location downstream of the first location. The first on-line analyzer is configured to provide information relating to the measured inhibitor concentration at the second location to the first controller, the first controller configured to process the information from the first on-line analyzer and to adjust at least a first operating parameter of a first addition device if the measured inhibitor concentration at the second location is outside a first predetermined condition. A second controller and a second on-line analyzer are provided to provide similar control of water addition to acrylonitrile product.

15 Claims, 2 Drawing Sheets

ON-LINE ANALYSIS OF ACRYLONITRILE PRODUCT

FIELD OF THE INVENTION

The invention relates to an improved process for the manufacture of acrylonitrile and methacrylonitrile. In particular, the invention is directed to improved processes that include improved monitoring of product quality to ensure that product meets predetermined specifications.

BACKGROUND

Various processes and systems for the manufacture of acrylonitrile and methacrylonitrile are known; see for example, U.S. Pat. No. 6,107,509. As noted in U.S. Pat. No. 6,107,509, conventional processes typically involve recovery and purification of acrylonitrile/methacrylonitrile produced by the direct reaction of a hydrocarbon selected from the group consisting of propane, propylene or isobutylene, ammonia and oxygen in the presence of a catalyst has been accomplished by transporting the reactor effluent containing acrylonitrile/methacrylonitrile to a first column (quench) where the reactor effluent is cooled with a first aqueous stream, transporting the cooled effluent containing acrylonitrile/methacrylonitrile into a second column (absorber) where the cooled effluent is contacted with a second aqueous stream to absorb the acrylonitrile/methacrylonitrile into the second aqueous stream, transporting the second aqueous stream containing the acrylonitrile/methacrylonitrile from the second column to a first distillation column (recovery column) for separation of the crude acrylonitrile/methacrylonitrile from the second aqueous stream, and transporting the separated crude acrylonitrile/methacrylonitrile to a second distillation column (heads column) to remove at least some impurities from the crude acrylonitrile/ methacrylonitrile, and transporting the partially purified acrylonitrile/methacrylonitrile to a third distillation column (product column) to obtain product acrylonitrile/methacrylonitrile. U.S. Pat. Nos. 4,234,510; 3,885,928; 3,352,764; 3,198,750 and 3,044,966 are illustrative of typical recovery and purification processes for acrylonitrile and methacrylonitrile.

It is important for acrylonitrile product to meet specifications, including the maximum amount of certain chemical impurities, and predetermined amounts of water and polymerization inhibitor. Control of the water and polymerization content of acrylonitrile product is important to the stability of the acrylonitrile product. The amount of water and monomethyl ether hydroquinone or methyl ether of hydroquinone (hereinafter "MEHQ") polymerization inhibitor in acrylonitrile product typically must be maintained within specified levels or ranges. The MEHQ polymerization inhibitor requires a certain amount of water in order to function and inhibit undesirable polymerization of acrylonitrile product. Specifications, such as U.S. and international shipping specifications, typically require a minimum amount of water and inhibitor in the acrylonitrile product to be shipped because the acrylonitrile product without a certain amount of water and inhibitor is highly reactive. Specifications typically have a maximum amount of water and inhibitor content as well because excessive water and inhibitor will make desired subsequent reaction of acrylonitrile slow and difficult, e.g., at a customer plant designed to polymerize acrylonitrile. Specifications for the acrylonitrile product typically have maximums on certain impurities, such as hydrogen cyanide, acetonitrile, and acetone.

A conventional process has the following steps. First, acrylonitrile product from the final distillation column is accumulated in one of two or more product rundown tanks. These tanks are equipped with mixers, and have provision for addition of water and MEHQ polymerization inhibitor. Next, a sample is taken of the acrylonitrile product that has accumulated in the rundown tank. Next, this sample is analyzed in the laboratory for water content, MEHQ content, and other product specifications. If the water in the acrylonitrile is below the specified amount, a calculation is made on the amount of water that must be added in order to meet the specification. This amount of water is then added manually to the rundown tank. Likewise, if the MEHQ in the acrylonitrile is below the specified amount, a calculation is made on the amount of MEHQ solution that must be added in order to meet the specification. This amount of MEHQ solution is then added manually to the rundown tank. The rundown tank is then mixed for a specified period of time.

After mixing, the acrylonitrile in the rundown tank is re-sampled. This second sample is analyzed in the laboratory for water content, MEHQ content, and other product specifications. If analysis of the sample of acrylonitrile in the rundown tank indicates that the contents meet the specifications, the acrylonitrile is then transferred from the rundown tank to one of the final product storage tanks. The above conventional process requires multiple rundown tanks so that acrylonitrile can be produced continuously while the steps listed above are completed. The conventional process includes the need to make final adjustments to water and MEHQ content in at least one rundown tank, and multiple steps that require time to complete before acrylonitrile product is brought within specification and can be released to final product storage. The conventional process requires plant and laboratory time and labor for the drawing of samples in the plant, transferring the drawn samples to the laboratory, analyzing the samples in the laboratory, relaying the laboratory analysis to plant operators, determining of action based on the laboratory analysis, and the taking of action in the plant in an attempt to bring the product in the at least one rundown tank within specification. In some instances, multiple steps may not be accomplished in sufficient time for taking of corrective action at the rundown tank. In such instances, an amount of product in the rundown tank must then be re-run through equipment upstream of the rundown in an attempt to bring the product to within specification. The conventional process typically requires at least three rundown tanks, wherein there is filling of a first tank with acrylonitrile product, analyzing of acrylonitrile product in a second tank that was previously filled, with no flow of acrylonitrile product entering or exiting from the second tank during the step analyzing, and pumping acrylonitrile product out of third tank after filling and analyzing of acrylonitrile product in the third tank was completed.

SUMMARY

Accordingly, an aspect of the disclosure is to provide a safe, effective and cost effective method and apparatus that overcomes or reduces the disadvantages of conventional processes.

In an aspect, the apparatus comprises a first location wherein a polymerization inhibitor is added to an acrylonitrile product to form a mixture of acrylonitrile product and the polymerization inhibitor. The apparatus further comprises a first controller, the first controller configured to control at least the flow rate of a polymerization inhibitor to the first location, or at least the flow rate of the acrylonitrile product to the first location. The apparatus further comprises a first on-line analyzer, the first on-line analyzer configured to measure polymerization inhibitor concentration in the acrylonitrile product at a second location, the second location downstream of the first location. The first on-line analyzer is configured to provide information relating to the measured inhibitor concentration at the second location to the first controller, the first controller configured to process the information from the first on-line analyzer and to adjust at least a first operating parameter if the measured inhibitor concentration at the second location is outside a first predetermined condition.

In an aspect, the apparatus comprises a third location wherein water is added to the acrylonitrile product to form a mixture of acrylonitrile product and water. The apparatus comprises a second controller, the second controller configured to control at least the flow rate of water to the third location, or at least the flow rate of the acrylonitrile product to the third location. The apparatus further comprises a second on-line analyzer, the second on-line analyzer configured to measure water concentration in the acrylonitrile product at a fourth location, the fourth location downstream of the third location. The second on-line analyzer is configured to provide information relating to the measured water concentration at the third location to the second controller, the second controller configured to process the information from the second on-line analyzer and to adjust at least a second operating parameter if the measured water concentration at the fourth location is outside a second predetermined condition.

The above and other aspects, features and advantages of the present disclosure will be apparent from the following detailed description of the illustrated embodiments thereof which are to be read in connection with the accompanying drawings.

BRIEF DESCRIPTION OF THE DRAWING

A more complete understanding of the exemplary embodiments of the present invention and the advantages thereof may be acquired by referring to the following description in consideration of the accompanying drawings in which like reference numbers indicate like features and wherein.

DETAILED DESCRIPTION

Figure 1:
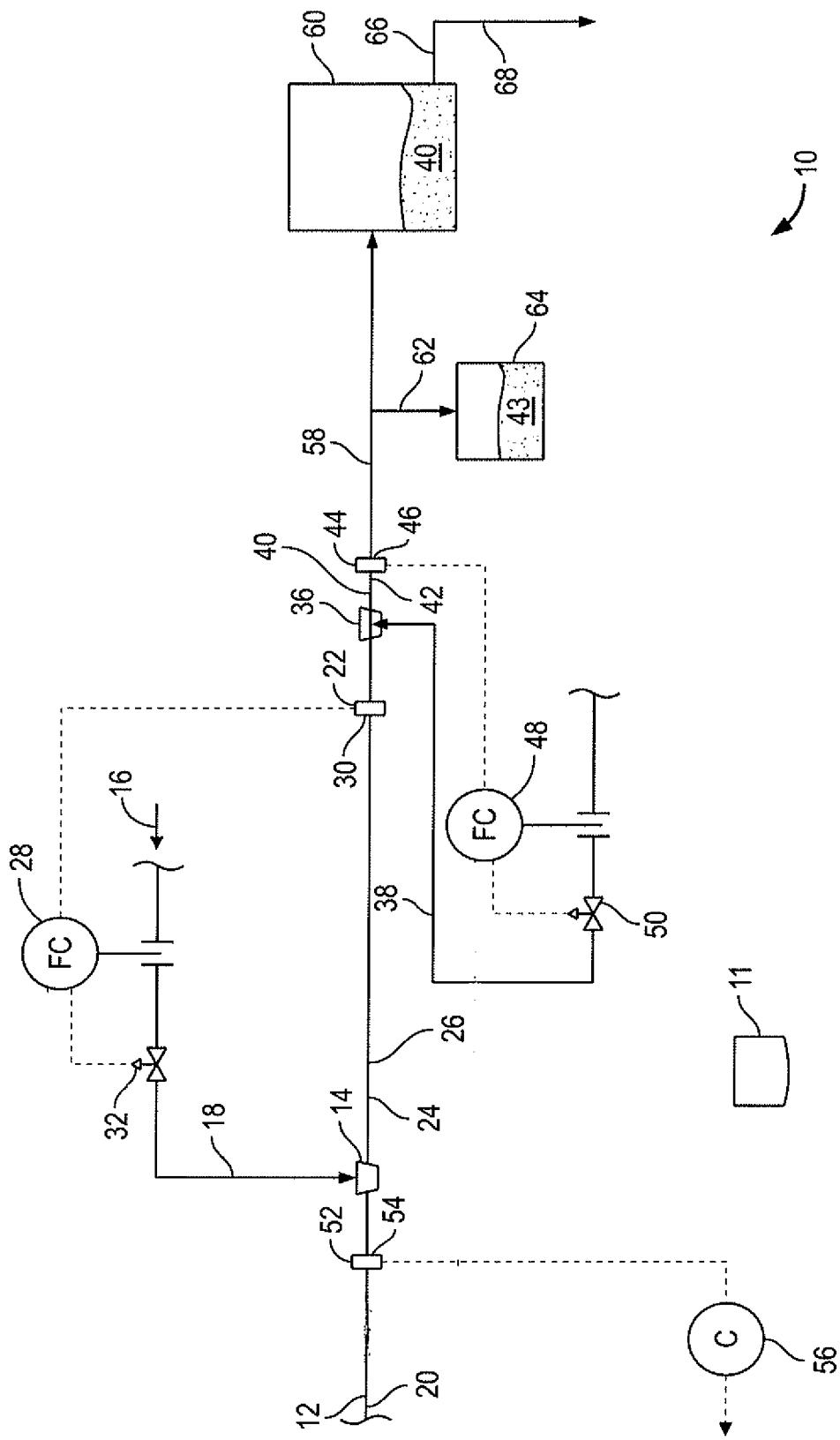
FIG. 1 is a schematic flow diagram of an embodiment in accordance with aspects of the disclosure as applied to the manufacture of acrylonitrile product.

The process and apparatus of the present disclosure is described in detail with reference to FIG. 1.

Apparatus 10 is downstream of a product column (not shown in FIG. 1) used in an acrylonitrile manufacturing process. Purified or relatively purified acrylonitrile product 20 from a product column may be received in conduit or line 12 of apparatus 10. Line 12 may include a juncture location or juncture 14. Juncture 14 may be configured to receive a polymerization inhibitor 16 via line 18. At juncture 14, polymerization inhibitor 16 may be added to the purified or relatively purified acrylonitrile product 20. Juncture 14 may be any suitable conduit or vessel configured to receive the purified or relatively purified acrylonitrile product 20 from a product column Polymerization inhibitor 16 may be any suitable polymerization inhibitor that inhibits the polymerization of acrylonitrile product. By way of example, but not limitation, the polymerization inhibitor 16 may comprise monomethyl ether hydroquinone or methyl ether of hydroquinone (hereinafter "MEHQ"). As shown in FIG. 1, mixture 24 of product 20 and polymerization inhibitor 16 flows from juncture 14 through line 26.

Line 26 flows to analyzer 22. Analyzer 22 may be configured to analyze mixture 24 in line 26 at location 30, which is downstream of juncture 14. Analyzer 22 may be configured to measure the concentration of inhibitor 16 in mixture 24. Analyzer 22 may be an on-line or in-line analyzer that is configured to continuously sample and analyze the concentration of inhibitor 16 in mixture 24. Analyzer 22 may be any suitable analyzer configured to measure the concentration of inhibitor 16 in mixture 24. For example, analyzer 22 may be an ultraviolet light (UV) analyzer. Analyzer 22 may be configured to provide information relating to the measured inhibitor concentration to controller 28. Controller 28 may be configured to process the information from analyzer 22 and to adjust at least a first operating parameter if the measured inhibitor concentration at location 30 is outside a predetermined condition. Controller 28 may include a processor. The processor of controller 28 may comprise a memory configured to receive and store the predetermined condition. The predetermined condition may be a value or range of desired inhibitor concentration in mixture 24.

For example, the predetermined condition stored in memory of controller 28 may be a concentration of inhibitor 16 in mixture 24 of $X \pm 0.02X$. If analyzer 22 measures the actual concentration to be $X-0.03X$ or lower, then controller 28 processes the actual concentration information from analyzer 22, and adjusts at least a first operating parameter to increase the inhibitor concentration since the measured inhibitor concentration at location 30 is below the predetermined condition of concentration of inhibitor 16 in mixture 24. The first operating parameter may be the size of the opening of valve 32 on line 18. Thus, when the measured inhibitor concentration at location 30 is below the predetermined condition, then controller 28 adjusts the opening of valve 32 so that it becomes larger to increase the addition of inhibitor 16 at junction 14 to product 20 by an appropriate amount, and thus increase the concentration of inhibitor 16 in mixture 24 exiting junction 14 by an appropriate amount. When the measured inhibitor concentration at location 30 is above a predetermined condition of concentration of inhibitor 16 in mixture 24 (e.g., $X+0.03X$ or higher), then controller 28 adjusts the opening of valve 32 so that it becomes smaller to decrease the addition of inhibitor 16 at junction 14 to product 20 by an appropriate amount, and thus decrease the concentration of inhibitor 16 in mixture 24 exiting junction 14 by an appropriate amount. Those skilled in the art will recognize that in accordance with the disclosure, analyzer 22 may be used for feedback control of inhibitor addition, and allowing for continuous production of mixture or end acrylonitrile product 40 or 66, further discussed below, which meets the specification amount of inhibitor concentration in end acrylonitrile product 40 or 66. In the above example, the specification concentration amount or range of inhibitor in mixture or acrylonitrile end product 40 or 66 may be $X \pm 0.04X$. Thus, apparatus and method of the present disclosure provides for feedback control of inhibitor addition, wherein the inhibitor concentration in the acrylonitrile product 40 or 66 is maintained within the specification concentration amount or range, e.g., $X \pm 0.04X$ in the above example.

In an embodiment, controller 28 may adjust the opening of valve 32 by an appropriate amount to bring the concentration of inhibitor 16 in mixture 24 within the predetermined condition. Those skilled in the art will recognize that in accordance with the disclosure, analyzer 22 may be used for feedback control of inhibitor addition and/or amount of acrylonitrile product to be mixed with inhibitor, and allowing for continuous production of end acrylonitrile product 40 and/or 66 that meets the specification amount or range of inhibitor concentration in end acrylonitrile product 40 and/or 66.

Line 26 may comprise a juncture location or juncture 36. Juncture 36 may be configured to receive water via line 38. At juncture 36, water may be added to the mixture 24 flowing in line 26 to form mixture 40 exiting juncture 36. Juncture 36 may be any suitable conduit or vessel configured to receive mixture 24 flowing from line 26. The water added at juncture 36 may be for example, demineralized water, RO water, or distilled water. As shown in FIG. 1, mixture 40 flows from juncture 36 through line 42.

Line 42 flows to analyzer 44. Analyzer 44 may be configured to analyze mixture 40 in line 42 at location 46, which is downstream of juncture 36. Analyzer 44 may be configured to measure the concentration of water in mixture 40. Analyzer 44 may be an on-line or in-line analyzer that is configured to continuously sample and analyze the concentration of water in mixture 40. Analyzer 44 may be any suitable analyzer configured to measure the concentration of water in mixture 40. For example, analyzer 44 may be an infrared light (IR) analyzer. Analyzer 44 may be configured to provide information relating to the measured water concentration to controller 48. Controller 48 may be configured to process the information from analyzer 44 and to adjust at least a second operating parameter if the measured water concentration at location 46 is outside a predetermined condition. Controller 48 may comprise a processor. The processor of controller 48 may comprise a memory configured to receive and store the predetermined condition. The predetermined condition may be a value or range of desired water concentration in mixture 40.

For example, the predetermined condition stored in memory of controller 48 may be a concentration of water in mixture 40 of Y+0.02Y. If analyzer 44 measures the actual concentration to be Y+0.01Y or lower, then controller 48 processes the actual concentration information from analyzer 44, and adjusts at least a second operating parameter to increase the water concentration since the measured water concentration at location 46 is below the predetermined condition of concentration of water in mixture 40. The second operating parameter may be the size of the opening of valve 50 on line 38. Thus, when the measured water concentration at location 46 is below the predetermined condition, then controller 48 adjusts the opening of valve 50 so that it becomes larger to increase the addition of water at junction 36 to mixture 24 by an appropriate amount, and thus increase the concentration of water in mixture 40 exiting junction 36 by an appropriate amount. When the measured water concentration at location 46 is above a predetermined condition of concentration of water in mixture 40 (e.g., Y+0.03Y or higher), then controller 48 adjusts the opening of valve 50 so that it becomes smaller to decrease the addition of water at junction 36 to mixture 24 by an appropriate amount, and thus decrease the concentration of water in mixture 40 exiting junction 36 by an appropriate amount. Those skilled in the art will recognize that in accordance with the disclosure, analyzer 44 may be used for feedback control of water addition, and allowing for continuous production of mixture or end acrylonitrile product 40 or 66, further discussed below, which meets the specification amount of water concentration in end acrylonitrile product 40 or 66. In the above example, the specification amount of water concentration in mixture or acrylonitrile end product 40 or 66 may be Y±0.04Y. Thus, apparatus and method of the present disclosure provides for feedback control of water addition, wherein the water concentration in the acrylonitrile product 40 or 66 is maintained within the specification concentration amount or range, e.g., Y±0.04Y in the above example.

In an embodiment, controller 48 may adjust the opening of valve 50 by an appropriate amount to ultimately bring the concentration of water in end acrylonitrile product or mixture 40 within the predetermined condition. Those skilled in the art will recognize that in accordance with the disclosure, analyzer 44 may be used for feedback control of water addition and/or amount of acrylonitrile product to be mixed with water, and allowing for continuous production of mixture 40 and/or end acrylonitrile product 66 that meets the specification concentration amount of water concentration in mixture 40 and/or acrylonitrile product 66.

As shown in FIG. 1, line 12 of apparatus 10 may comprise analyzer 52. Analyzer 52 may be configured to analyze acrylonitrile product 20 from an acrylonitrile product column at location 54. Analyzer 52 may be configured to detect or measure the concentration of at least one chemical impurity in acrylonitrile product 20, e.g., at least one impurity selected from the group consisting of hydrogen cyanide, acetonitrile, and acetone. Analyzer 52 may be an on-line or in-line analyzer that is configured to continuously sample and analyze the presence or concentration of at least chemical impurity in acrylonitrile product 20. Analyzer 52 may be any suitable analyzer. For example, analyzer 52 may be a gas chromatograph (GC) analyzer. Analyzer 52 may be configured to provide information relating to the detected or measured impurity concentration to controller 56. Controller 56 may be configured to process the information from analyzer 52 and to adjust at least a third operating parameter if the detected or measured impurity concentration at location 54 is outside a predetermined condition. Controller 56 may comprise a processor. The processor of controller 56 may comprise a memory configured to receive and store the third predetermined condition. The third predetermined condition may be a value or range of maximum impurity concentration in acrylonitrile product 20. Those skilled in the art will recognize that in accordance with the disclosure, the controller 56 may adjust one or more operating parameters upstream of location 54 to reduce the presence or amount of a chemical impurity in acrylonitrile product 20.

For example, the predetermined condition stored in memory of controller 56 may be a concentration of hydrogen cyanide in acrylonitrile product 20 of Z+0.02Z. If analyzer 52 measures the actual concentration of hydrogen cyanide in acrylonitrile product 20 at location 54 to be greater (e.g., Z+0.03Z or higher), then controller 56 adjusts an operating parameter upstream of location 54 to reduce hydrogen cyanide in acrylonitrile product 20, e.g., an operating parameter of a heads column to reduce the amount of hydrogen cyanide in partially purified acrylonitrile product before entering the product column for further purification. Those skilled in the art will recognized that the apparatus and method of the present disclosure provides early detection of any component that may go off specification or approach going off specification, thereby allowing for corrective action to be taken and minimizing the amount of acrylonitrile that may need to be re-run through any portion (s) of an acrylonitrile manufacturing plant. Those skilled in the art will recognize that in accordance with the disclosure, analyzer 52 may be used for feedback control of upstream operating parameters, and allowing for continuous production of acrylonitrile product that meets the specification amount of impurities in that acrylonitrile product. In the above example, the specification amount of an impurity concentration in mixture or acrylonitrile end product 40 and/or 66 may be a maximum of Y+0.04Y. Thus, apparatus and method of the present disclosure provides for feedback control, wherein the impurity concentration in the acrylonitrile product 40 and/or 66 is maintained within or below the specification concentration amount or range, e.g., Y+0.04Y in the above example.

As shown in FIG. 1, when mixture 40 meets the specification amounts or ranges for inhibitor, water and impurities, e.g., as measured by analyzers 22, 44, and 52, respectively, then mixture 40 may be allowed to flow through line 58 to tank 60. Tank 60 may be a rundown tank and/or a storage tank. Portion 43 of mixture 40 may flow through line 62 to a composite sample collector 64. Collector 64 may be configured to collect portion 43 of mixture 40 that is representative of a period of acrylonitrile production, e.g., a period of several hours, such as three to twelve hours. Sample portion 43 collected in collector 64 may be analyzed in a laboratory to verify the on-line or in-line analyzer results of analyzers 22, 44 and 52.

Mixture 40 collected in tank 60 may be distributed as end acrylonitrile product 66 through line 68. For example, end acrylonitrile product 66 may be placed in a final product tank that is certified for filling shipping containers (not shown) after sample portion 43 has been analyzed in a laboratory to verify the on-line or in-line analyzer results of analyzers 22, 44 and 52, and/or sample portion 43 meets the specification concentration amounts or ranges for inhibitor and water, and meets or is below the specification concentration amounts or ranges for impurities in mixture 40 and/or end acrylonitrile product 66. The contents of a final product tank may be analyzed and certified before the product is transferred to a shipping port or shipping containers.

While analyzers 22, 44, and 52 are shown in FIG. 1 to be on the product line, those skilled in the art will recognize that in accordance with the disclosure the analyzers may be located at one or more slip streams off the product line. Each slip stream may comprise a booster pump.

Those of skill in the art will recognize that at least the following benefits are provided by the present disclosure. A benefit provided by the present disclosure is that the on-line or in-line analysis of acrylonitrile product for inhibitor and/or water allow for inhibitor and/or water addition to be put on closed-loop control. These features may eliminate the need to make final adjustments to water and inhibitor (e.g., MEHQ) content in at least one rundown tank, including mixing of water and inhibitor with acrylonitrile product in the at least one rundown tank.

One benefit provided by the present disclosure is that acrylonitrile product that is off-specification for chemical impurities may be detected sooner, allowing corrective action to be taken and reducing the amount of acrylonitrile product re-run through a portion(s) of the system to as required in conventional systems and methods. Other benefits provided by the present disclosure are less time and fewer steps may be required before acrylonitrile product is released to final product storage than in conventional systems and methods. Both laboratory and plant labor may be reduced in carrying out analysis of samples and adjustments to operating parameters to produce acrylonitrile product that is within specifications. Other benefits provided by the present disclosure are that the number and/or volume of the rundown tanks may be decreased over the number and/or volume of rundown tanks required in conventional systems and methods.

In accordance with an embodiment of the disclosure, the on-line acrylonitrile product analysis system may comprise the following components and provide the following benefits:

A gas chromatograph (GC) is used to continuously analyze for chemical impurities. This analysis provides early detection of any component that may go off specification, thereby allowing corrective action to be taken and minimizing the amount of acrylonitrile that may need to be re-run through at least one column or vessel of an acrylonitrile production plant.

A UV analyzer is used to measure the inhibitor (e.g., MEHQ) concentration in the acrylonitrile. For example, this analyzer may be used for feedback control of inhibitor solution addition, allowing continuous production of acrylonitrile that meets the specification concentration value or range for the inhibitor.

An IR analyzer is used to measure the water content of the acrylonitrile. The acrylonitrile purification process typically produces acrylonitrile that has less water than the specification requires, so the on-line analyzer is used for feedback control of demineralized water addition. This allows for continuous production of acrylonitrile that meets the specification for water content.

A composite sample collector is used to collect an acrylonitrile sample that is representative of several hours of acrylonitrile production. This sample can be analyzed in the laboratory to verify the on-line analyzer results.

The sample collection and distribution system may provide continuous flow of acrylonitrile product to the analysis systems described herein.

In an aspect, controller 11 may be configured to process one or more signals corresponding to a measured parameter. Controller 11 may be configured to determine whether the measured parameter is above or below a predetermined parameter range. Controller 11 may be configured to adjust operation of one or more devices via communication lines or wireless communications (not shown in FIG. 1) if the measured parameter is below or above a predetermined parameter range. Those skilled in the art will recognize that controller 11 or a similar controller may be located remote from controller 28, controller 48, and/or controller 56 (as shown in FIG. 1), or may be located at and comprise controller 28, controller 48, or controller 56.

Figure 2:
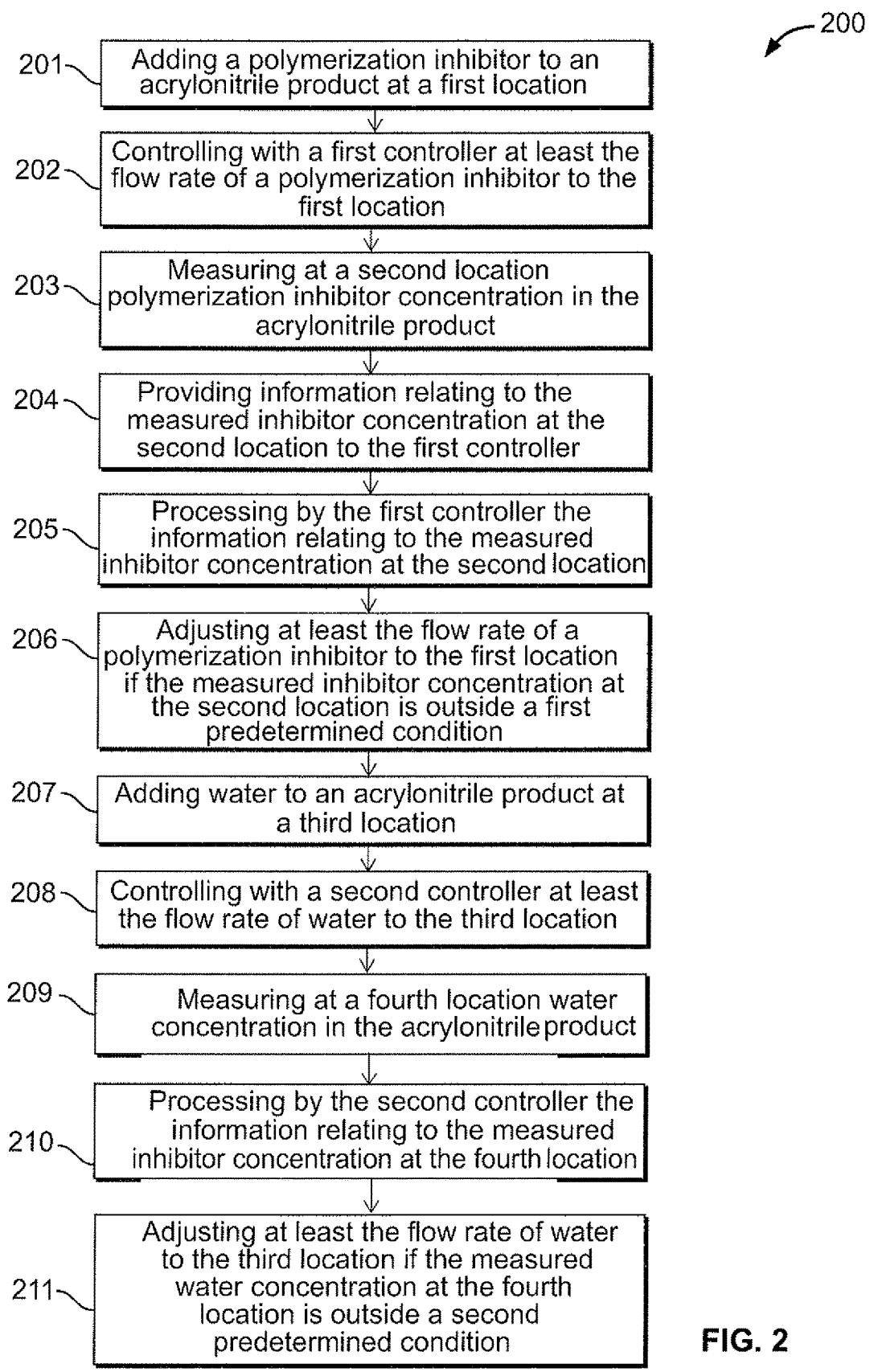
FIG. 2 illustrates a flow diagram of a method in accordance with aspects of the disclosure.

FIG. 2 illustrates a flow diagram of a method 200 in accordance with aspects of the disclosure. Step 201 comprises adding a polymerization inhibitor to an acrylonitrile product at a first location to form a mixture of acrylonitrile product and the polymerization inhibitor. Step 202 comprises controlling with a first controller at least the flow rate of a polymerization inhibitor to the first location, or at least the flow rate of the acrylonitrile product to the first location. Step 203 comprises measuring at a second location polymerization inhibitor concentration in the acrylonitrile product, the second location downstream of the first location. Step 204 comprises providing information relating to the measured inhibitor concentration at the second location to the first controller. Step 205 comprises processing by the first controller the information relating to the measured inhibitor concentration at the second location. Step 206 comprises adjusting at least the flow rate of a polymerization inhibitor to the first location or at least the flow rate of the acrylonitrile product to the first location if the measured inhibitor concentration at the second location is outside a first predetermined condition. Step 207 comprises adding water to an acrylonitrile product at a third location to form a mixture of acrylonitrile product and water. Step 208 comprises controlling with a second controller at least the flow rate of water to the third location, or at least the flow rate of the acrylonitrile product to the third location. Step 209 comprises measuring at a fourth location water concentration in the acrylonitrile product, the fourth location downstream of the third location. Step 210 comprises processing by the second controller the information relating to the measured inhibitor concentration at the fourth location. Step 211 comprises adjusting at least the flow rate of water to the third location or at least the flow rate of the acrylonitrile product to the third location if the measured water concentration at the fourth location is outside a second predetermined condition.

While in the foregoing specification this disclosure has been described in relation to certain preferred embodiments thereof, and many details have been set forth for purpose of illustration, it will be apparent to those skilled in the art that the disclosure is susceptible to additional embodiments and that certain of the details described herein can be varied considerably without departing from the basic principles of the disclosure. It should be understood that the features of the disclosure are susceptible to modification, alteration, changes or substitution without departing from the spirit and scope of the disclosure or from the scope of the claims. For example, the dimensions, number, size and shape of the various components may be altered to fit specific applications. Accordingly, the specific embodiments illustrated and described herein are for illustrative purposes only.

We claim:

1. An apparatus comprising:

a first location wherein a polymerization inhibitor is added to an acrylonitrile product to form a mixture of acrylonitrile product and the polymerization inhibitor;

a first controller, the first controller configured to control at least the flow rate of a polymerization inhibitor to the first location, or at least the flow rate of the acrylonitrile product to the first location, wherein the first controller comprises a first processor, the first processor comprising a first memory, the first memory configured to receive and store the first predetermined condition;

a first on-line analyzer, the first on-line analyzer configured to measure polymerization inhibitor concentration in the acrylonitrile product at a second location, the second location downstream of the first location;

the first on-line analyzer configured to provide information relating to the measured inhibitor concentration at the second location to the first controller, the first controller configured to process the information from the first on-line analyzer and to adjust at least a first operating parameter of a first addition device if the measured inhibitor concentration at the second location is outside a first predetermined condition;

a third location wherein water is added to the acrylonitrile product to form a mixture of acrylonitrile product and water;

a second controller, the second controller configured to control at least the flow rate of water to the third location, or at least the flow rate of the acrylonitrile product to the third location, wherein the second controller comprises a second processor, the second processor comprising a second memory, the second memory configured to receive and store the second predetermined condition;

a second on-line analyzer, the second on-line analyzer configured to measure water concentration in the acrylonitrile product at a fourth location, the fourth location downstream of the third location;

the second on-line analyzer configured to provide information relating to the measured water concentration at the fourth location to the second controller, the second controller configured to process the information from the second on-line analyzer and to adjust at least a second operating parameter of a second addition device if the measured water concentration at the fourth location is outside a second predetermined conditions;

a third controller, the third controller configured to control at least one operating parameter of an acrylonitrile manufacturing plant, wherein the third controller comprises a third processor, the third processor comprising a third memory, the third memory configured to receive and store the third predetermined condition;

a third on-line analyzer, the third on-line analyzer configured to measure at least one impurity concentration in the acrylonitrile product at a fifth location, the fifth location upstream of the first location; wherein the third on-line analyzer comprises a gas chromatograph;

the third on-line analyzer configured to provide information relating to the measured at least one impurity at the fifth location to the third controller, the third controller configured to process the information from the third on-line analyzer and to adjust at least a third operating parameter upstream of the fifth location if the measured impurity concentration at the fifth location is greater than a third predetermined condition; and a composite sample collector located at a sixth location, the sixth location downstream of the fourth location, the composite sample collector configured to collect a sample representative of three to twelve hours of acrylonitrile production.

2. The apparatus of claim 1, wherein the polymerization inhibitor is methyl ether of hydroquinone.

3. The apparatus of claim 1, wherein the first on-line analyzer comprises an ultraviolet light analyzer.

4. The apparatus of claim 1, wherein the first predetermined condition comprises a desired inhibitor concentration at the second location.

5. The apparatus of claim 4, wherein the first addition device is selected from the group consisting of a valve, pump, and combinations thereof.

6. The apparatus of claim 5, wherein the first addition device is configured to be operated for controlled addition of inhibitor to the acrylonitrile product at the first location.

7. The apparatus of claim 5, wherein the first addition device is configured to be operated for controlled addition of acrylonitrile product to inhibitor at the first location.

8. The apparatus of claim 1, wherein the second on-line analyzer comprises an infrared light analyzer.

9. The apparatus of claim 1, wherein the second predetermined condition comprises a desired water concentration at the fourth location.

10. The apparatus of claim 9, wherein the second addition device is selected from the group consisting of a valve, pump, and combinations thereof.

11. The apparatus of claim 10 wherein the second addition device is configured to be operated for controlled addition of water to the acrylonitrile product at the third location.

12. The apparatus of claim 10, wherein the second addition device is configured to be operated for controlled addition of acrylonitrile product to water at the third location.

13. The apparatus of claim 1, wherein the third predetermined condition comprises a desired maximum concentration of the at least one impurity at the fifth location.

14. The apparatus of claim 13, wherein the first addition device is selected from the group consisting of a valve, pump, and combinations thereof.

15. The apparatus of claim 1, wherein the at least one impurity is selected from the group consisting of hydrogen cyanide, acetonitrile, and acetone, and combinations thereof.

* * * * *